United States Patent [19]

Edwards

[11] 4,259,104
[45] Mar. 31, 1981

[54] HERBICIDAL AND PLANT-GROWTH-REGULATING 2-PHENOXYALKYL-OXADIAZOLES

[75] Inventor: Laroy H. Edwards, Napa, Calif.

[73] Assignee: Chevron Research Company, San Francisco, Calif.

[21] Appl. No.: 53,878

[22] Filed: Jul. 2, 1979

[51] Int. Cl.³ .................... A01N 43/82; C07D 271/10
[52] U.S. Cl. .......................................... 71/92; 548/144
[58] Field of Search ....................... 548/144; 71/88, 92

[56] References Cited

U.S. PATENT DOCUMENTS 3,947,263   3/1976   Brouwer et al. ...................... 71/88

FOREIGN PATENT DOCUMENTS

Ad.82869   4/1964   France .................................. 548/144
474952   7/1969   Switzerland .............................. 71/88

OTHER PUBLICATIONS

Sen Gupta, et al., "J. Indian Chem. Soci.", vol. 32, (1975) pp. 1084–1085.
Dornow et al., "Chem. Ber.", vol. 82, (1949), pp. 121–123.
Hoggarth, "J. Chem. Soci." (London) 1952, pp. 4811–4817.

Giri, et al., "Agr. Biol. Chem.", vol. 140(1), 1976, pp. 17–21.

Primary Examiner—Anton H. Sutto
Attorney, Agent, or Firm—D. A. Newell; T. G. DeJonghe; R. J. Suyat

[57] ABSTRACT

Compounds of the formula

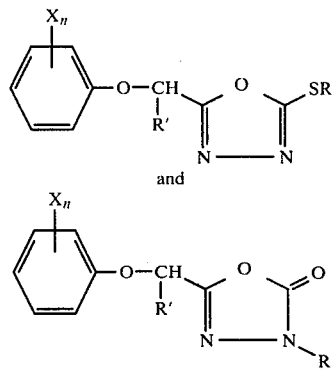

wherein X is halo or $C_1$–$C_4$ alkyl, n = 1, 2 or 3 and R and R' are hydrogen or $C_1$–$C_6$ alkyl have herbicidal and plant-growth regulating activity.

10 Claims, No Drawings

HERBICIDAL AND PLANT-GROWTH-REGULATING 2-PHENOXYALKYL-OXADIAZOLES

BACKGROUND OF THE INVENTION

SenGupta et al. disclose 2-(4-pent-3-yl)phenoxymethyl-5-arylamino-1,3,4-oxadiazoles in *J. Indian Chem. Soc.*, 32, pp. 1084–5 (1975).

Dornow et al. disclose 2-alkyl-1,3,4-oxadiazol-5-one derivatives in *Chem. Ber.*, 82, pp. 121–3 (1949).

Hoggarth discloses 2-mercapto-5-phenyl-1,3,4-oxadiazole derivatives in *J. Chem. Soc.* 1952, pp. 4811–17.

SUMMARY OF THE INVENTION

The present invention relates to novel herbicidal compounds, compositions and methods of use thereof. It has been found that certain 4- and 5-substituted 2-(aryloxymethyl)-1,3,4-oxadiazoles have herbicidal and plant-growth regulating activity. The compounds of the invention are generally effective in both pre- and post-emergent applications and are particularly selective in post-emergent applications against broad-leaved plants.

DESCRIPTION OF THE INVENTION

The compounds of the invention are represented by the formula (I):

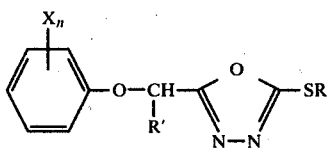

and by the formula (Ia):

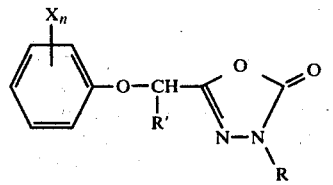

wherein n is 1, 2 or 3 and X is the same or different group selected from bromo, chloro, fluoro, iodo or alkyl of 1 to 4 carbon atoms; R and R' are individually hydrogen or alkyl of 1 to 6 carbon atoms.

Representative X groups are bromo, chloro, fluoro, iodo, methyl, ethyl, i-propyl, n-propyl, n-butyl, i-butyl, sec-butyl. Preferably X is halo. Most preferably n is 2 and both X groups are chloro.

Representative R and R' groups are hydrogen, methyl, ethyl, i-propyl, n-propyl, n-butyl, n-pentyl, i-pentyl, i-hexyl, etc. Preferably R is alkyl of 1 to 6 carbon atoms. Most preferably R is methyl.

Preferably R' is hydrogen.

The compounds of the invention may be made according to the following scheme:

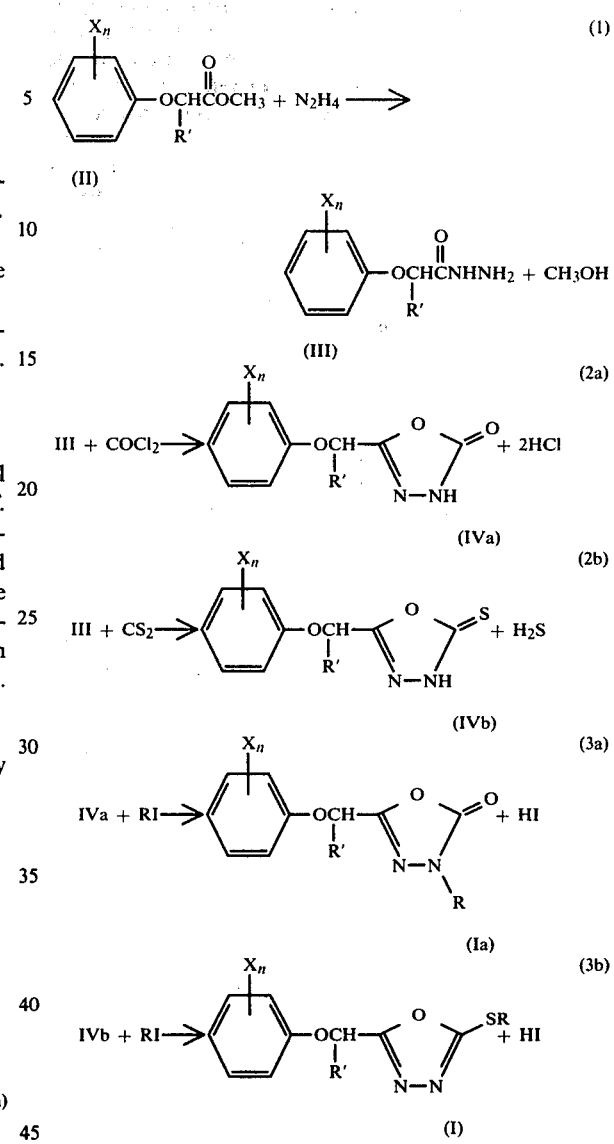

Reaction (1) may be conducted at room temperature in a suitable solvent, preferably water, by mixing substantially eqimolar amounts of the ester (II) and hydrazine.

Reaction (2a) may be conducted at about 10°–90° C. in a suitable inert solvent. Preferably the reaction is conducted by refluxing equimolar amounts of the hydrazide (III) and phosgene in a solvent, such as benzene. Thus equivalents of a base, such as a trialkylamine, may be added as a scavenger for the hydrogen chloride which is evolved.

Reaction (2b) may be conducted under general conditions similar to that of reaction (2a), i.e., reaction of equimolar amounts of the hydrazide (III) and carbon disulfide in a solvent, such as DMF, at reflux temperature.

Reactions (3a) and (3b) are conventional alkylations using an alkyl iodide.

Utility

The compounds of the present invention are, in general, herbicidal in both pre- and post-emergent applications. For pre-emergent control of undesirable vegetation, the herbicidal compounds will be applied in herbicidally effective amounts of the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broad-leaved weeds. Some may be selective with respect to the type of application and/or type of weed. The compounds are particularly effective as post-emergent herbicides against broad-leaved plants.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredient usually makes up from 0.5–90% of these powder compositions. The solids ordinarily should be very finely divided. For conversion of the powders to dusts, talc, pyrophyllite, and the like, are customarily used. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wettings, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

the amount of compound or composition administered will vary with the particular plant part or plant growth medium which is to be contacted, the general location of application—i.e., sheltered areas such as greenhouse, as compared to exposed areas such as fields—as well as the desired type of control. Generally for both pre- and post-emergent herbicidal control, the compounds of the invention are applied at rates of 0.2 to 60 kg/ha, and the preferred rate is in the range 0.5 to 40 kg/ha. For plant growth regulating or retarding activity, it is essential to apply the compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal and plant-growth-regulating tests on representative compounds of the invention were made using the following methods.

Pre-Emergent Herbicidal Test

An acetone solution of the test compound was prepared by mixing 375 mg of the compound, 118 mg of a nonionic surfactant and 18 ml of acetone. 10 ml of this solution was added to 40 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table I.

Post-Emergent Herbicidal Test

The test compound was formulated in the same manner as described above for the pre-emergent test. This formulation was uniformly sprayed on 2 similar pots of 24-day-old plants (approximately 15 to 25 plants per pot) at a dose of 27.5 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table I.

AUXILIARY BUD GROWTH INHIBITION OF PINTO BEAN PLANTS

Compound Nos. 12 and 19 were tested to determine their plant-growth-retarding effects on axially bud growth of pinto beans.

Idaho pinto bean plants (13–16 days old) having monofoliate leaves fully developed and first trifoliates beginning to unfold were used. All growth 5 mm above the monofoliate leaf node was removed with forceps 1 to 4 hours prior to treatment with the test compounds. Four plants were used for each test compound.

A 625-ppm solution of the test compound in a 2% aqueous acetone solution containing a small amount of a non-ionic surfactant was sprayed onto the pinto bean plants until runoff. After drying, the treated plants were transferred to a greenhouse maintained at 20°–23° C. and watered at regular intervals. Twelve days after treatment, the bud growth at the axil of the monofoliate leaf was determined and expressed as percent inhibition of axillary bud growth as compared to untreated check plants. Compound 12 exhibited 100% inhibition and Compound 19 exhibit 93% inhibition.

COTTON DEFOLIATION TEST

Compound No. 3 was tested to determine its postemergent foliar activity for cotton defoliation and/or desiccation.

Cotton plants (26–35 days old) with 4 fully expanded leaves were used. Two days before use, the growth beyond the 4th leaf was removed.

A 5000-ppm solution of the test compound in acetone containing a small amount of a nonionic surfactant was sprayed on two cotton plants until runoff. The treated plants were transferred to a greenhouse maintained at 23°–25° C. The plants were watered from the base 1–2 times per day using an automatic sub-irrigation system. Ten days after treatment the percent defoliation and desiccation was determined (relative to the original number of mature leaves). The results for Compound No. 3 were 88% defoliation and 5% desiccaion.

ROOT INITIATION AND ELONGATION OF BEAN CUTTINGS

Uniform size pinto bean plants (variety Idaho) about 10–14 days old were cut 5 cm. below the cotyledons. The cotyledons and one of the monofoliates were removed and the cut end was placed in a brown bottle of an aqueous nutrient solution containing the test compound and a concentration of 0.5 ppm. The bottles were held at room temperature (72°–75° F.) under fluorescent lights set for 12-hour photoperiods. Periodic observations of root initiation (number of roots formed) are made for a period of 10–12 days, with 0 indicating no roots formed and 100 indicating the plant treated with the standard (IBA) having the greatest number of roots. Root initiation is recorded when the root length is greater than its width.

Compound 3 exhibited the root initiation value of 100.

ROOT INHIBITION OF MUNG BEAN AND WATERGRASS SEEDLINGS

Ten mung bean seeds and ten watergrass seeds were placed in each of several Northrup-King Seed-Pack growth pouches. To each pouch was added 15 ml. of a 40 ppm aqueous solution of the test compound. The pouches were suspended in containers under 125–150 foot-candles of light for six days at room temperature. Root length is measured for each species and expressed as percent inhibition compound to check samples treated with the standard MH-30.

Compound 19 exhibited root inhibition of 44% for watergrass and 86% for mung beans.

EXAMPLE 1—Preparation of 2-(2-methyl-4-chlorophenoxymethyl)-4-methyl-1,3,4-oxadiazol-5-one A. Methyl (2-methyl-4-chlorophenoxy)acetate (60 g.) in 200 ml water was stirred while adding an aqueous solution of hydrazine (18 g.). After stirring at room temperature overnight, the water was decanted. The solid residue was stirred with methylene chloride, filtered and dried at room temperature to yield 29 g of the hydrazide (IA).

B. To 32.2 g of the hydrazide (IA) in benzene (50 ml), was added dropwise a 12.5% solution of phosgene (120 g) in benzene. After stirring overnight at room temperature two equivalents of triethylamine were added and the solution was refluxed for 2 hours. The mixture was washed with water, dried (MgSO$_4$) and stripped to yield 10 g (purified by chromatograhy) of 2-(2-methyl-4-chlorophenoxymethyl)-1,3,4-oxadiazol-5-one (IB).

C. To IB (4.0 g) in acetone was added 1.1 g K$_2$CO$_3$ and the mixture was refluxed for 2 hours. After cooling 2.4 g methyl iodide was added and the solution was refluxed for one hour. The mixture was filtered, stripped, slurried in water and extracted with methylene chloride. The methylene chloride solution was dried and stripped to yield 3.2 g of the title product, m.p. 108°–110° C.

EXAMPLE 2—Preparation of 2-(2-methyl-4-chlorophenoxymethyl)-5-methylthio-1,3,4-oxadizole A. The hydrazide (IA, 28.8 g), carbon disulfide (51.0 g) and dimethylformamide (50 ml) were combined and heated at reflux for 4 hours. The mixture was added to ice water, the water was decanted and the solids were slurried in methylene chloride. The methylene chloride mixture was filtered, the solids were dried at room temperature and recrystallized in benzene/pet. ether.

Purification (chromatography) yielded (2-(2-methyl-4-chlorophenoxymethyl)-1,3,4-oxadiazol-5-thione (IIA).

B. The thione (IIA, 26.7 g) was treated as in Example IC with K$_2$CO$_3$ (7.2 g) and methyl iodide (14.8 g) in acetone (200 ml) to yield 15 g of the title product, m.p. 56°–57° C.

EXAMPLE 3—Preparation of 2-(2,4-dichlorophenoxymethyl)-5-methylthio-1,3,4-oxadizole A. Following the procedure of Example IIA, 2,4-dichlorophenoxyacetic acid hydrazide (23.5 g) and carbon disulfide (38 g) in DMF (50 ml) were reacted and worked up to yield 2-(2,4-dichlorophenoxymethyl)-1,3,4-oxadiazol-5-thione (IIIA).

B. IIIA (11.7 g), methyl iodide (6 g) and K$_2$CO$_3$ (2.9 g) in acetone (200 ml) were treated according to Example IC to yield 8.3 g of the title compound, m.p. 60°–62° C.

TABLE A

COMPOUNDS OF THE FORMULA

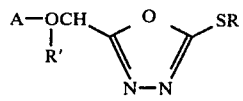

| No. | A | R | R' | mp. °C. | S Cal. | S Fd. | Cl Cal. | Cl Fd. |
|---|---|---|---|---|---|---|---|---|
| 1 | 2,4-Cl$_2$—φ | H | H | 141–143 | 11.57 | 11.3 | 25.59 | 24.3 |
| 2 | (2-CH$_3$)—4-Cl—φ | H | H | 165–166 | 12.49 | 11.4 | 13.81 | 13.6 |
| 3 | 2,4-Cl$_2$—φ | CH$_3$ | H | 60–62 | 11.01 | 11.1 | 24.36 | 23.6 |
| 4 | (2-CH$_3$)—4-Cl—φ | CH$_3$ | H | 56–57 | 11.84 | 10.9 | 13.09 | 13.8 |
| 5 | 2,5-Cl$_2$—φ | H | H | 132–134 | 11.57 | 11.1 | 25.09 | 25.5 |
| 6 | 2,5-Cl$_2$—φ | CH$_3$ | H | 109–111 | 11.01 | 10.8 | 24.36 | 24.4 |
| 7 | 2,5-Cl$_2$—φ | CH(CH$_3$)$_2$ | H | 70–72 | 10.04 | 9.7 | 22.21 | 21.7 |
| 8 | 2,4-Cl$_2$—φ | C$_2$H$_5$ | H | 50–51 | 10.51 | 10.1 | 23.24 | 23.3 |
| 9 | 2,4-Cl$_2$—φ | CH(CH$_3$)$_2$ | H | oil | 10.04 | 10.3 | 22.21 | 23.4 |
| 10 | 2,4,5-Cl$_3$—φ | H | H | 180–182 | 10.29 | 10.3 | 34.14 | 33.8 |
| 11 | 2,4,5-Cl$_3$—φ | CH$_3$ | H | 115–117 | 9.85 | 10.0 | 32.66 | 32.3 |
| 12 | 2,4,5-Cl$_3$—φ | CH(CH$_3$)$_2$ | H | 101–102 | 9.07 | 10.0 | 30.08 | 29.8 |
| 13 | 4-Br—φ | C$_2$H$_5$ | H | 55–56 | 10.17 | 10.4 | 25.35 | 23.5 |
| 14 | 4-Br—φ | CH$_3$ | H | 47–49 | 10.65 | 11.2 | 26.54 | 26.5 |
| 15 | 4-Br—φ | H | H | 171–173 | 11.17 | 11.4 | 27.84 | 28.5 |
| 16 | 2,4-Cl$_2$—φ | H | CH$_3$ | 100–102 | 11.01 | 10.2 | 24.36 | 25.3 |
| 17 | 2,4-Cl$_2$—φ | CH$_3$ | CH$_3$ | oil | 10.51 | 10.4 | 23.24 | 23.0 |
| 18 | 2,4-Cl$_2$—φ | C$_2$H$_5$ | CH$_3$ | oil | 10.04 | 10.2 | 22.21 | 22.3 |
| 19 | 3,4-Cl$_2$—φ | CH$_3$ | H | 78–80 | 38.84[1] | 39.08[1] | 3.26[2] | 3.19[2] 9.06[3] 8.28[3] |

[1] Carbon
[2] Hydrogen
[3] Nitrogen

TABLE B

COMPOUNDS OF THE FORMULA

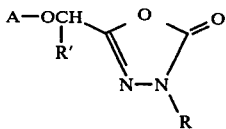

| No. | A | R | R' | mp. °C. | Cl Cal. | Cl Fd. |
|---|---|---|---|---|---|---|
| 20 | 2,4-Cl$_2$-φ | H | H | 140–142 | 27.17 | 26.5 |
| 21 | (2-CH$_3$)-4-Cl-φ | H | H | 140–142 | 14.73 | 15.7 |
| 22 | (2-CH$_3$)-4-Cl-φ | CH$_3$ | H | 108–110 | 13.92 | 13.8 |

TABLE I

HERBICIDAL ACTIVITY
% Control Pre/Post

| No. | L | M | P | C | W | O |
|---|---|---|---|---|---|---|
| 1 | 100/95 | 100/100 | 100/45 | 85/0 | 65/0 | 35/0 |
| 2 | 100/0 | 90/0 | 100/0 | 10/0 | 0/0 | 0/0 |
| 3 | 0/70 | 0/70 | 0/60 | 0/0 | 0/0 | 0/0 |
| 4 | 65/95 | 65/100 | 60/95 | 45/45 | 10/40 | 35/30 |
| 5 | 0/60 | 0/40 | 0/40 | 0/0 | 0/0 | 0/0 |
| 6 | 0/0 | 0/0 | 0/0 | 0/0 | 0/0 | 0/0 |
| 7 | 0/40 | 0/20 | 0/25 | 0/25 | 0/0 | 0/10 |
| 8 | 80/85 | 65/93 | 90/87 | 30/0 | 0/0 | 25/0 |
| 9 | 70/85 | 40/80 | 75/90 | 0/10 | 0/10 | 20/0 |
| 10 | 85/80 | 50/85 | 55/70 | 0/0 | 0/0 | 0/0 |
| 11 | 0/87 | 0/80 | 0/60 | 0/0 | 0/0 | 0/0 |
| 12 | 0/85 | 0/80 | 0/70 | 0/0 | 0/0 | 0/0 |
| 13 | 0/60 | 0/60 | 0/45 | 0/0 | 0/0 | 0/0 |
| 14 | 0/70 | 0/80 | 0/60 | 0/0 | 0/0 | 0/0 |
| 15 | 0/50 | 0/50 | 0/50 | 0/0 | 0/0 | 0/0 |
| 16 | 45/70 | 70/70 | 40/65 | 0/0 | 0/0 | 0/0 |
| 17 | 0/50 | 0/50 | 0/20 | 0/0 | 0/0 | 0/0 |
| 18 | 0/65 | 0/30 | 0/25 | 0/0 | 0/0 | 0/0 |
| 19 | 65/90 | 70/90 | 80/80 | 0/0 | 0/0 | 0/0 |
| 20 | 65/75 | 90/— | 100/90 | 92/0 | 65/0 | 20/0 |
| 21 | 100/40 | 100/90 | 100/15 | 97/0 | 100/0 | 40/0 |

TABLE I-continued

HERBICIDAL ACTIVITY
% Control Pre/Post

| No. | L | M | P | C | W | O |
|---|---|---|---|---|---|---|
| 22 | 100/80 | 100/90 | 100/70 | 100/0 | 100/0 | 25/0 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avenua fatua*)

What is claimed is:

1. A compound of the formula

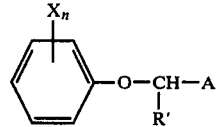

wherein A is

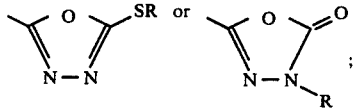

X is the same or different group selected from bromo, chloro, fluoro, iodo or alkyl of 1 to 4 carbon atoms; n is 2 or 3; R and R' are individually hydrogen or alkyl of 1 to 6 carbon atoms; with the proviso that when n=2 and neither X group is alkyl of 1 to 4 carbon atoms, the X groups are not at the and 2 and 5 positions of the phenyl ring.

2. A method for retarding plant growth which comprises appling to said plants or their growth environment a plant-growth-retarding amount of the compound of the formula defined in claim 1.

3. A plant-growth-regulating or retarding composition comprising a biologically inert carrier and a plant-growth-regulating or retarding amount of the compound of the formula defined in claim 1.

4. A compound of claim 1 wherein X is bromo, chloro, fluoro or iodo.

5. A compound of claim 4 wherein X is chloro.

6. A compound of claim 5 wherein A is

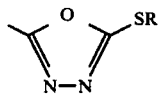

7. A compound of claim 5 wherein A is

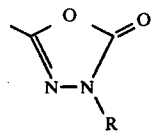

8. A compound according to claim 6 wherein n=2, R' is hydrogen and R is alkyl of 1 to 6 carbon atoms.

9. The compound 2-(2,4-dichlorophenoxymethyl)-5-methylthio-1,3,4-oxadiazole, according to claim 8.

10. The compound 2-(3,4-dichlorophenoxymethyl)-5-methylthio-1,3,4-oxadiazole, according to claim 8.

* * * * *